(12) United States Patent
Ishimizu et al.

(10) Patent No.: US 11,793,648 B2
(45) Date of Patent: Oct. 24, 2023

(54) PROSTHETIC JOINT AND MANUFACTURING METHOD FOR SAME

(71) Applicant: KYOCERA Corporation, Kyoto (JP)

(72) Inventors: Keita Ishimizu, Kyoto (JP); Mitsuyoshi Yamashita, Kyoto (JP); Takeshi Sumitani, Kyoto (JP)

(73) Assignee: KYOCERA Corporation, Kyoto (JP)

( * ) Notice: Subject to any disclaimer, the term of this patent is extended or adjusted under 35 U.S.C. 154(b) by 317 days.

(21) Appl. No.: 17/269,681

(22) PCT Filed: Aug. 16, 2019

(86) PCT No.: PCT/JP2019/032143
§ 371 (c)(1),
(2) Date: Feb. 19, 2021

(87) PCT Pub. No.: WO2020/040051
PCT Pub. Date: Feb. 7, 2020

(65) Prior Publication Data
US 2021/0322176 A1    Oct. 21, 2021

(30) Foreign Application Priority Data

Aug. 23, 2018 (JP) ................ 2018-156119

(51) Int. Cl.
*A61F 2/36* (2006.01)
*A61F 2/30* (2006.01)

(52) U.S. Cl.
CPC .......... *A61F 2/3609* (2013.01); *A61F 2/3094* (2013.01); *A61F 2/30767* (2013.01);
(Continued)

(58) Field of Classification Search
CPC ............ A61F 2002/30321; A61F 2/367; A61F 2/3676; A61F 2/30767; A61F 2250/0025
See application file for complete search history.

(56) References Cited

U.S. PATENT DOCUMENTS

| | | | | |
|---|---|---|---|---|
| 7,497,875 B1 * | 3/2009 | Zweymuller | ............ | A61F 2/36 623/23.35 |
| 2003/0158554 A1 * | 8/2003 | Hall | .................... | A61C 8/0022 438/584 |

(Continued)

FOREIGN PATENT DOCUMENTS

| | | | | |
|---|---|---|---|---|
| EP | 2868297 A1 | 5/2015 | | |
| FR | 2923375 A1 * | 5/2009 | ......... | A61F 2/30771 |

(Continued)

OTHER PUBLICATIONS

International Search Report and Written Opinion for the International Application No. PCT/JP2019/032143, dated Oct. 29, 2019, 14 pages.

*Primary Examiner* — Javier G Blanco
(74) *Attorney, Agent, or Firm* — PROCOPIO CORY HARGREAVES AND SAVITCH LLP

(57) ABSTRACT

Provided is an artificial joint that can improve fatigue strength while achieving the ability to fix to a bone. An artificial joint 1 includes a stem portion 2. The stem portion 2 has a distal end for insertion into a bone and a proximal end opposite the distal end and includes a roughened surface portion 4 which is provided in a proximal end-side portion, which has a rougher surface than a distal end-side portion, and which is larger in cross-sectional area than the distal end-side portion. The roughened surface portion 4 includes a distal end-side edge section 7 and a proximal end-side section 7, the distal end-side edge section 7 including a distal end-side edge portion of the roughened surface portion 4, the proximal end-side section 7 being configured as a section closer to the proximal end than the distal end-side edge section 7 is to the proximal end. The distal end-side edge section 7 has a surface roughness Ra1 lower than a surface roughness Ra2, Ra3 of the proximal end-side section.

6 Claims, 10 Drawing Sheets

(52) U.S. Cl.
CPC ............ *A61F 2/367* (2013.01); *A61F 2/3676* (2013.01); *A61F 2002/30067* (2013.01); *A61F 2002/30321* (2013.01); *A61F 2002/30971* (2013.01); *A61F 2310/00023* (2013.01); *A61F 2310/00407* (2013.01)

(56) References Cited

U.S. PATENT DOCUMENTS

| | | | |
|---|---|---|---|
| 2008/0221681 A1 | 9/2008 | Trieu et al. | |
| 2014/0343685 A1* | 11/2014 | Ranawat | A61F 2/3662 623/23.35 |
| 2015/0196397 A1* | 7/2015 | Slater | A61F 2/3662 623/23.29 |

FOREIGN PATENT DOCUMENTS

| | | |
|---|---|---|
| JP | 10-155822 A | 6/1998 |
| JP | 3318407 B2 | 8/2002 |
| WO | 2001/076653 A1 | 10/2001 |
| WO | 2015/107841 A1 | 7/2015 |

* cited by examiner

FIG. 4

| | Slope angle θ (degree) | Surface roughness (μm) | | Results of stem fatigue test | |
|---|---|---|---|---|---|
| | | Distal end-side edge section Ra1 | Proximal end-side second section Ra3 | Runout load (kN) | Location of breakage |
| Comparative Example 1 | 54 | 25 | 21 | 2.1 | Thermally sprayed layer's distal portion |
| Comparative Example 2 | 82 | 48 | 45 | 2.1 | Thermally sprayed layer's distal portion |
| Comparative Example 3 | 28 | 37 | 32 | 2.3 | Surface of thermally sprayed layer in a region where cross-sectional area is greater than that at the distal end of the thermally sprayed layer by not more than 7% |
| Comparative Example 4 | 22 | 16 | 12 | 3.2 | No breakage |
| Example 1 | 19 | 27 | 53 | 2.6 | Surface of thermally sprayed layer in a region where cross-sectional area is greater than that at the distal end of the thermally sprayed layer by not more than 7% |
| Example 2 | 31 | 18 | 47 | 2.9 | Surface of thermally sprayed layer in a region where cross-sectional area is greater than that at the distal end of the thermally sprayed layer by not more than 7% |
| Example 3 | 11 | 12 | 51 | 2.9 | Surface of thermally sprayed layer in a region where cross-sectional area is greater than that at the distal end of the thermally sprayed layer by not more than 7% |

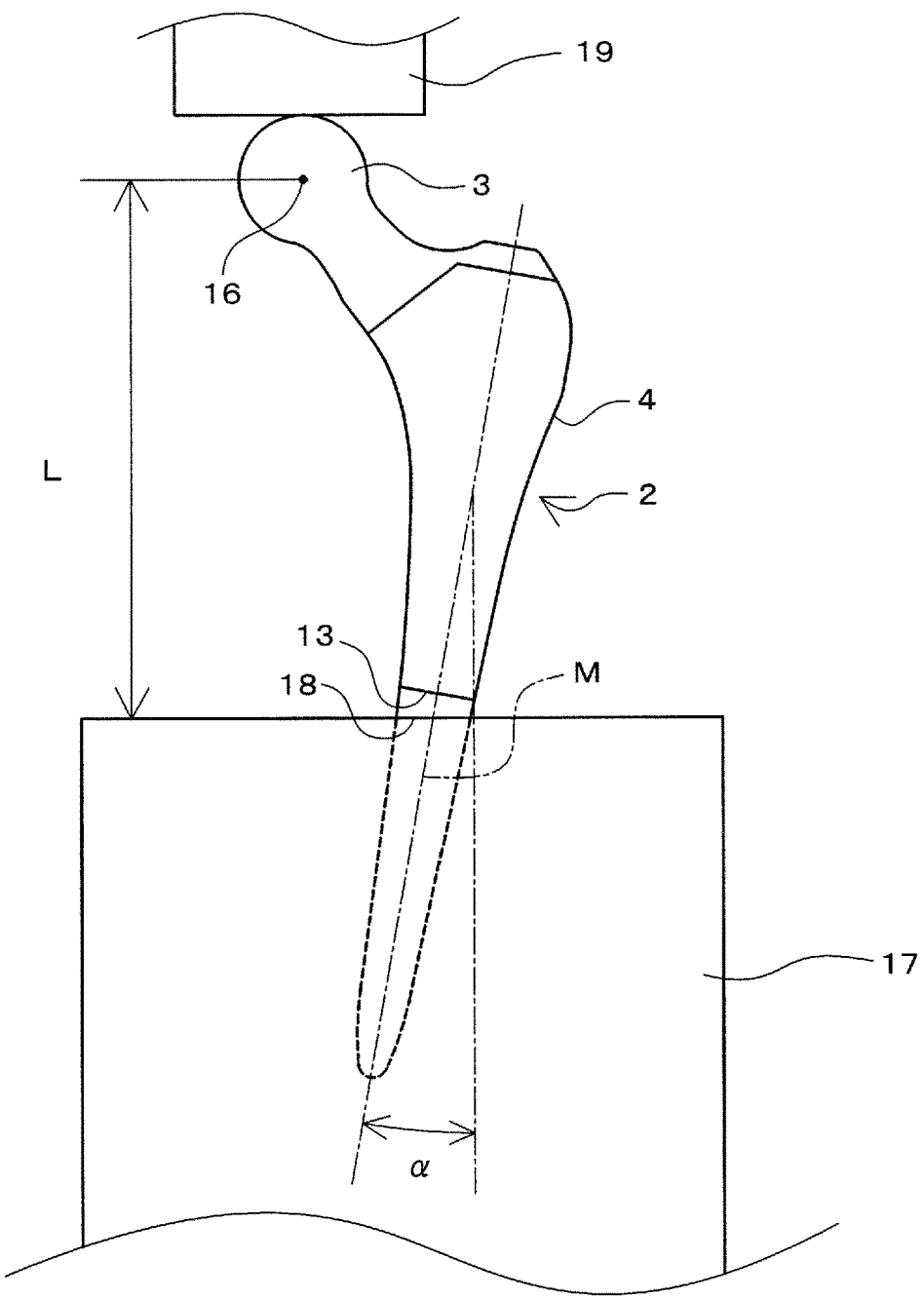

FIG. 7

| | | |
|---|---|---|
| Setting angle | Adduction | 10° ±1.0° |
| | Flexion | 9° ±1.0° |
| Fixing medium | PMMA cement (GC ostron, Surgical Simplex) | |
| Distance L from center-of-ball to fixing end | 80 mm ± 2 mm | |
| Test environment | Air at room temperature | |
| Pitch of load | When applied load is less than 2.3 kN: 0.2 kN | |
| | When applied load is 2.3 kN or more: 0.3 kN | |
| Maximum load | 3.2 kN | |
| Stress ratio | 0.1 | |
| Waveform | Sinusoidal wave | |
| Frequency | 10 Hz | |
| Repeat count | When load for test is 2.3 KN: five-million times after test load (maximum load, minimum load) is reached | |
| | When load for test is not 2.3 KN: one-million times after test load (maximum load, minimum load) is reached | | ized
PROSTHETIC JOINT AND MANUFACTURING METHOD FOR SAME

TECHNICAL FIELD

The present invention relates to an artificial joint for placement in the medullary cavity of a bone. The present invention also relates to a method of producing the artificial joint.

BACKGROUND ART

An artificial joint which has a stem portion to be inserted and placed in the medullary cavity of a bone and which is fixed to the bone has been conventionally used. For the purpose of fixing such an artificial joint to a bone, the surface of the stem portion is partially roughened, and the artificial joint is fixed to the bone by a frictional force. Fixing of the artificial joint to a bone in such a case is achieved in the following manner: immediately after the insertion of the artificial joint into the bone, the artificial joint and the bone are fixed together because of the bone and the roughened surface portion fixed together by frictional resistance; and then, after surgery, new bone grows into the spaces in the roughened surface portion as time passes, thereby fixing the artificial joint firmly to the bone.

One known method to roughen the surface in such a case is, for example, thermal spraying, which involves forming a coating layer by spraying molten particles of titanium or the like onto a substrate such as a metal substrate or a ceramic substrate. Other known methods of roughening the surface are, for example, fiber-mesh coating, bead coating, additive fabrication, and the like.

For example, Patent Literature 1 discloses an artificial hip joint in which the surface of the stem thereof is roughened by spraying, with a thermal spray gun, molten titanium to the stem rotatably placed in a chamber. Patent Literature 2 discloses a biological implant material on which molten titanium has been sprayed, whose ability to fix to a bone has been improved. Such artificial joints employ special configurations such as increased surface roughness, in order to improve the ability to fix to a bone.

CITATION LIST

Patent Literature

[Patent Literature 1]
Japanese Patent Application Publication, Tokukaihei, No. 10-155822
[Patent Literature 2]
Japanese Patent No. 3318407

SUMMARY OF INVENTION

Technical Problem

However, generally, an artificial joint such as a biological implant material has an issue in that, when the artificial joint has a surface roughened by thermal spraying, the thickness of a part formed by thermal spraying increases, stress concentration occurs in an edge portion of the part formed by thermal spraying, and the edge portion becomes prone to breakage. For preventing the artificial joint from being broken by stress concentration, the following measure has been taken, for example: the edge portion of the part formed by thermal spraying is placed out of the position subject to the greatest load on the artificial joint and thereby breakage is avoided. Furthermore, for some artificial joints, there is body weight limitation so that accidental failure such as breakage will not occur. However, in a case where the edge portion of the part formed by thermal spraying is placed out of the position subject to the greatest load on the artificial joint, the roughened area of the artificial joint becomes not large enough, and the ability to fix to a bone may decrease. Furthermore, if there is body weight limitation, such an artificial joint can be used only in limited applications. Under such circumstances, there has been a demand for an artificial joint that can improve fatigue strength while achieving the ability to fix to a bone.

The present invention is to address the above issue, and an object thereof is to provide an artificial joint that can improve fatigue strength while achieving the ability to fix to a bone.

Solution to Problem (1) In order to attain the above object, an artificial joint including a stem portion in accordance with an aspect of the present invention is configured such that: the stem portion has a distal end for insertion into a bone and a proximal end opposite the distal end and includes a roughened surface portion which is provided in a proximal end-side portion, which has a rougher surface than a distal end-side portion, and which is larger in cross-sectional area than the distal end-side portion; the roughened surface portion includes a distal end-side edge section and a proximal end-side section, the distal end-side edge section including a distal end-side edge portion of the roughened surface portion, the proximal end-side section being configured as a section closer to the proximal end than the distal end-side edge section is to the proximal end; and the distal end-side edge section has a surface roughness lower than a surface roughness of the proximal end-side section.

With the configuration, the stem portion of the artificial joint includes the roughened surface portion, which has a rough surface. When the stem portion of the artificial joint is inserted into a bone, the stem portion is fixed by a frictional force. Furthermore, the roughened surface portion is configured such that the distal end-side edge section has a lower surface roughness than that of the proximal end-side section. With this, the artificial joint configured as described above makes it possible, as compared to a conventional artificial joint which is not configured such that the surface roughness is low in the distal end-side edge portion, to avoid the occurrence of cracking and breakage and the like in the distal end-side edge portion of the roughened surface portion. This makes it possible to improve fatigue strength. Furthermore, the edge portion of the roughened surface portion does not need to be displaced, and there is no need to provide body weight limitation for using the artificial joint. Since the artificial joint configured as described above is configured such that the roughness of the proximal end-side section is greater than that of the distal end-side edge section, a sufficient ability to fix to a bone can also be achieved.

Thus, it is possible to provide an artificial joint that can improve fatigue strength while achieving the ability to fix to a bone.

(2) It is preferable that the distal end-side edge portion of the roughened surface portion have a sloped surface sloping downward toward the distal end.

With the configuration, the sloped surface is provided in the distal end-side edge portion of the roughened surface portion such that the sloped surface slopes downward toward the distal end. With this, the distal end of the roughened surface portion does not have a stepped shape, and it is possible to further alleviate the concentration of stress in the edge portion of the roughened surface portion. As a result, the occurrence of cracking and breakage and the like in the roughened surface portion of the artificial joint are further avoided.

(3) It is preferable that: the proximal end-side section include a proximal end-side first section and a proximal end-side second section, the proximal end-side first section being a part of the proximal end-side section which part is adjacent to the distal end-side edge section, the proximal end-side second section being adjacent to the proximal end-side first section and being located on the opposite side of the proximal end-side first section from the distal end-side edge section; and a surface roughness of the proximal end-side first section change such that the surface roughness of the proximal end-side first section gradually increases from a roughness of a similar level to a surface roughness of the distal end-side edge section to a roughness of a similar level to a surface roughness of the proximal end-side second section in a direction from the distal end toward the proximal end.

With the configuration, the proximal end-side section includes the proximal end-side first section and the proximal end-side second section, the proximal end-side first section is adjacent to the distal end-side edge section, and the proximal end-side second section is adjacent to the proximal end-side first section and is located on the opposite side of the proximal end-side first section from the distal end-side edge section. Furthermore, the surface roughness of the proximal end-side first section changes such that it gradually increases from a roughness of a similar level to the surface roughness of the distal end-side edge section to a roughness of a similar level to the surface roughness of the proximal end-side second section. Thus, the surface roughness of the roughened surface portion, in the direction from the distal end toward the proximal end, is gradually changed instead of being abruptly changed, which makes it possible to avoid stress concentration. This makes it possible to further improve fatigue strength while achieving the ability to fix to a bone.

(4) It is preferable that: the roughened surface portion include, at a surface thereof, a thermally sprayed layer composed of a coating material; and in the distal end-side edge section, the thermally sprayed layer increase in thickness with decreasing distance to the proximal end to form the sloped surface.

With the configuration, the roughened surface portion includes the thermally sprayed layer composed of a coating material. That is, the thermally sprayed layer is formed by spraying the coating material in a molten state. Furthermore, in the distal end-side edge section of the roughened surface portion, the thermally sprayed layer increases in thickness with decreasing distance to the proximal end to form the sloped surface. By changing conditions in which the coating material in a molten state is sprayed, it is possible to form the thermally sprayed layer which has an adjusted thickness. Therefore, it is possible to easily form, in the roughened surface portion, the sloped surface sloping at an angle suitable for need, by adjusting thickness.

(5) It is preferable that a slope angle be not more than 45 degrees, the slope angle being an angle between a surface of a base member 2a of the stem portion 2, the surface being covered by the thermally sprayed layer, and a surface of a distal end-side portion of the thermally sprayed layer.

With the configuration, the slope angle, which is the angle between the surface of the base member of the stem portion covered by the thermally sprayed layer and the surface of the distal end-side portion of the thermally sprayed layer, is not more than 45 degrees. This makes it possible to further alleviate the concentration of stress in the edge portion of the roughened surface portion that would otherwise result from a large slope angle. As a result, the occurrence of cracking and breakage and the like in the roughened surface portion of the artificial joint are further avoided.

(6) It is preferable that: the surface roughness, calculated as arithmetic mean roughness, of the distal end-side edge section be not greater than 35 μm; and the surface roughness, calculated as arithmetic mean roughness, of the proximal end-side section be not less than 40 μm.

With the configuration, the surface roughness, calculated as arithmetic mean roughness, of the distal end-side edge section is not more than 35 μm. This makes it possible to further avoid the occurrence of cracking and breakage and the like in the distal end-side edge portion of the roughened surface portion. Furthermore, the surface roughness, calculated as arithmetic mean roughness, of the proximal end-side section is not less than 40 μm, that is, the surface roughness of the proximal end-side section is set to a value greater than the surface roughness of the distal end-side edge section. This makes it possible to achieve a greater ability of the stem portion to fix to a bone.

(7) It is preferable that the stem portion contain a titanium alloy and/or pure titanium.

With the configuration, the stem portion contains a titanium alloy and/or pure titanium. Therefore, because of the high strength and biocompatibility of a titanium alloy or pure titanium, a more suitable artificial joint can be obtained.

(8) It is preferable that the artificial joint be an implant of an artificial hip joint for a thigh bone.

With the configuration, the artificial joint in accordance with the present invention is, for example, an implant of an artificial hip joint for a thigh bone. An implant for an artificial hip joint in accordance with the present invention is an artificial joint which, after implanted in the human body, receives a large load repeatedly during, for example, ambulation activity. In this regard, the following advantage, which is a characteristic of the present invention, can be further utilized: fatigue strength can be improved while achieving the ability to fix to a bone.

(9) A method of producing an artificial joint in accordance with an aspect of the present invention is a method of producing an artificial joint that includes a stem portion having a distal end for insertion into a bone and a proximal end opposite the distal end, the method including: a base member preparing step including preparing a base member which is to be covered by a thermally sprayed layer composed of a coating material; a masking step including partially covering the base member with a masking material; and a roughened surface portion forming step including spraying the coating material in a molten state to form a roughened surface portion which is provided in a proximal end-side portion of the stem portion, which has a rougher surface than a distal end-side portion, and which is larger in cross-sectional area than the distal end-side portion, in the roughened surface portion forming step, in order to allow a distal end-side edge section including a distal end-side edge portion of the roughened surface portion to have a surface roughness lower than a surface roughness of a proximal end-side section which is configured as a section closer to the proximal end, when the coating material in the molten state is sprayed to the distal end-side edge section, one or more of the following conditions under which the coating material in the molten state is sprayed to the proximal end-side section are changed: a time for which the coating material in the molten state is sprayed; a temperature at which the coating material in the molten state is sprayed; and a pressure at which the coating material in the molten state is sprayed.

A method of producing an artificial joint includes: a base member preparing step including preparing a base member of a stem portion; a masking step including placing a masking material on a part of the base member; and a roughened surface portion forming step in which a coating material in a molten state is sprayed to a proximal end-side portion of the stem portion to form a roughened surface portion which has a rougher surface than a distal end-side portion. That is, the stem portion of the artificial joint includes the roughened surface portion which has a rough surface. The roughened surface portion can be produced such that the surface roughness of the distal end-side edge section is lower than that of the proximal end-side section. This makes it possible to appropriately produce an artificial joint that has improved fatigue strength and achieves the ability to fix to a bone.

(10) It is preferable that: in the masking step, the masking material, which masks the stem portion, overhang the stem portion in a cross section passing through a central axis of the stem portion; and a sloped surface be formed in the distal end-side edge portion of the roughened surface portion, the sloped surface sloping downward toward the distal end.

In the method of producing an artificial joint, in the masking step, the masking material masks the stem portion so as to overhang the stem portion, and the sloped surface sloping downward toward the distal end is formed in the distal end-side edge portion of the roughened surface portion. That is, it is possible to provide, in the distal end-side edge portion of the roughened surface portion, a sloped surface sloping downward toward the distal end. This makes it possible to provide an artificial joint in which the occurrence of cracking, breakage, and the like in the roughened surface portion are further avoided.

Advantageous Effects of Invention

The present invention makes it possible to provide an artificial joint that can improve fatigue strength while achieving the ability to fix to a bone, and a method of producing the artificial joint.

BRIEF DESCRIPTION OF DRAWINGS

FIG. 4 is a table showing a list of the results of a fatigue test concerning Comparative Examples and Examples of the present invention.

FIG. 5 illustrates the artificial joint which is set in a fatigue tester such that the artificial joint is inclined in the direction of adduction.

FIG. 7 is a table showing a list of conditions in which the fatigue test was carried out.

DESCRIPTION OF EMBODIMENTS

The following description will discuss embodiments of the present invention with reference to the drawings. Note that the present invention has use in a wide variety of applications as an artificial joint for placement in the medullary cavity of a bone.

Figure 1:
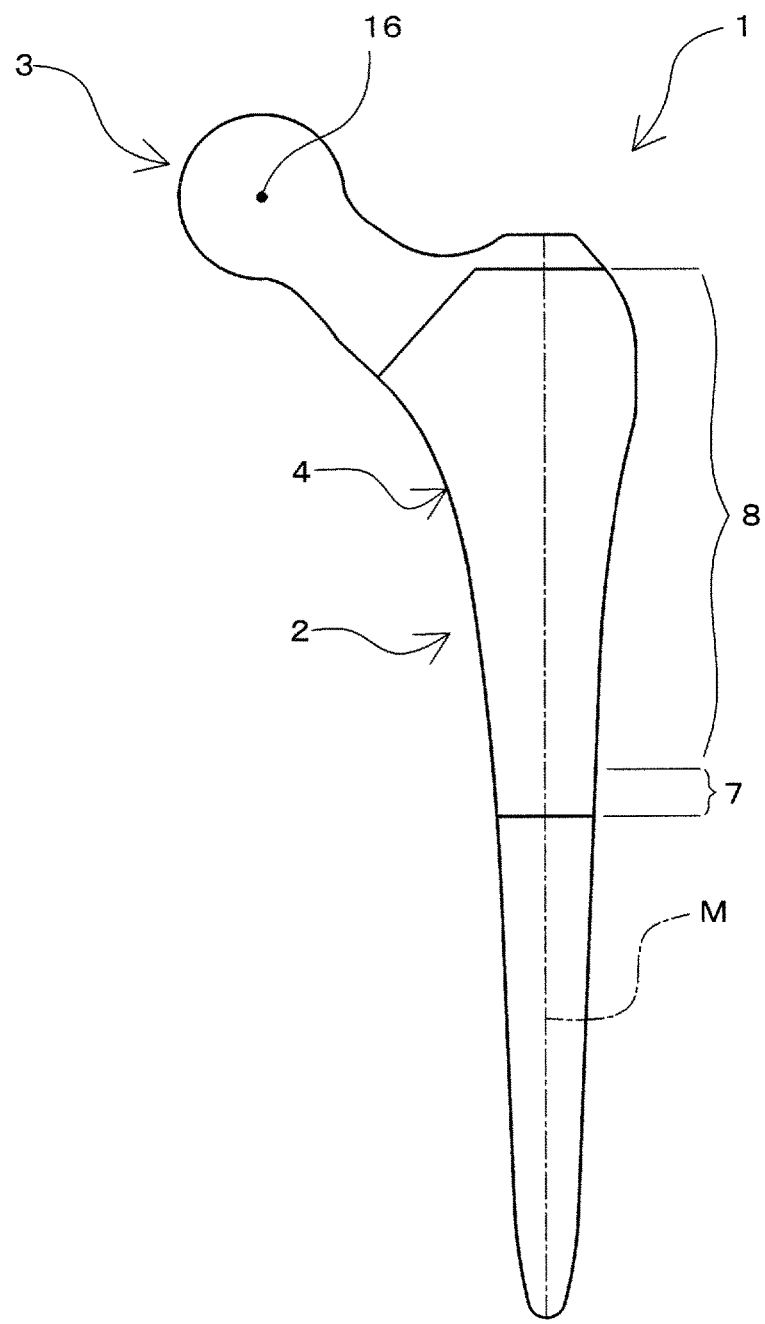
FIG. 1 illustrates an artificial joint in accordance with an embodiment of the present invention.

FIG. 1 illustrates an artificial joint 1 in accordance with an embodiment of the present invention. The artificial joint 1 includes: a stem portion 2 for placement in the medullary cavity of a bone; and a head ball portion 3 which is integral with the stem portion 2. The artificial joint 1 of the following embodiment relates to an implant of an artificial hip joint for a thigh bone.

The artificial joint 1 is attached to a thigh bone of a patient by artificial hip joint replacement. In the artificial hip joint replacement, an operator first cuts the femoral neck of the patient by osteotomy to remove the femoral neck, and uses a box chisel or the like to form a temporary hole in the medullary cavity of the thigh bone. Next, the operator shaves the temporary hole so as to spread it out, thereby forming an appropriate-size hole in the medullary cavity. Then, the operator inserts the stem portion 2 into the thus-formed hole in the medullary cavity and forcing it into the hole, thereby fixing the stem portion 2 to the medullary cavity. With this, the artificial joint 1, as a thigh bone-side implant of the artificial hip joint, is attached to the thigh bone. Then, the artificial joint 1 attached to the thigh bone is placed such that the head ball portion 3 of the artificial joint 1 slides on a pelvis-side implant of the artificial hip joint.

As described above, the artificial joint 1 in accordance with the present embodiment includes the stem portion 2 for insertion into the medullary cavity of a thigh bone. The stem portion 2 contains titanium alloy and/or pure titanium. The stem portion 2 is in a form that tapers from its proximal end to distal end. The stem portion 2 has: the distal end for insertion into the medullary cavity of a thigh bone; and the proximal end opposite the distal end. The stem portion 2 has, at the proximal end thereof, the head ball portion 3 integral with the stem portion 2. The stem portion 2 includes a roughened surface portion 4 which is provided in a proximal end-side portion (portion closer to the proximal end opposite the distal end for insertion into the bone than to the distal end) of the stem portion 2, which has a rougher surface than a distal end-side portion, and which is larger in cross-sectional area than the distal end-side portion. In a distal end-side area of the roughened surface portion 4 of the stem portion 2, the edge of the roughened surface portion 4 is located.

Figure 2:
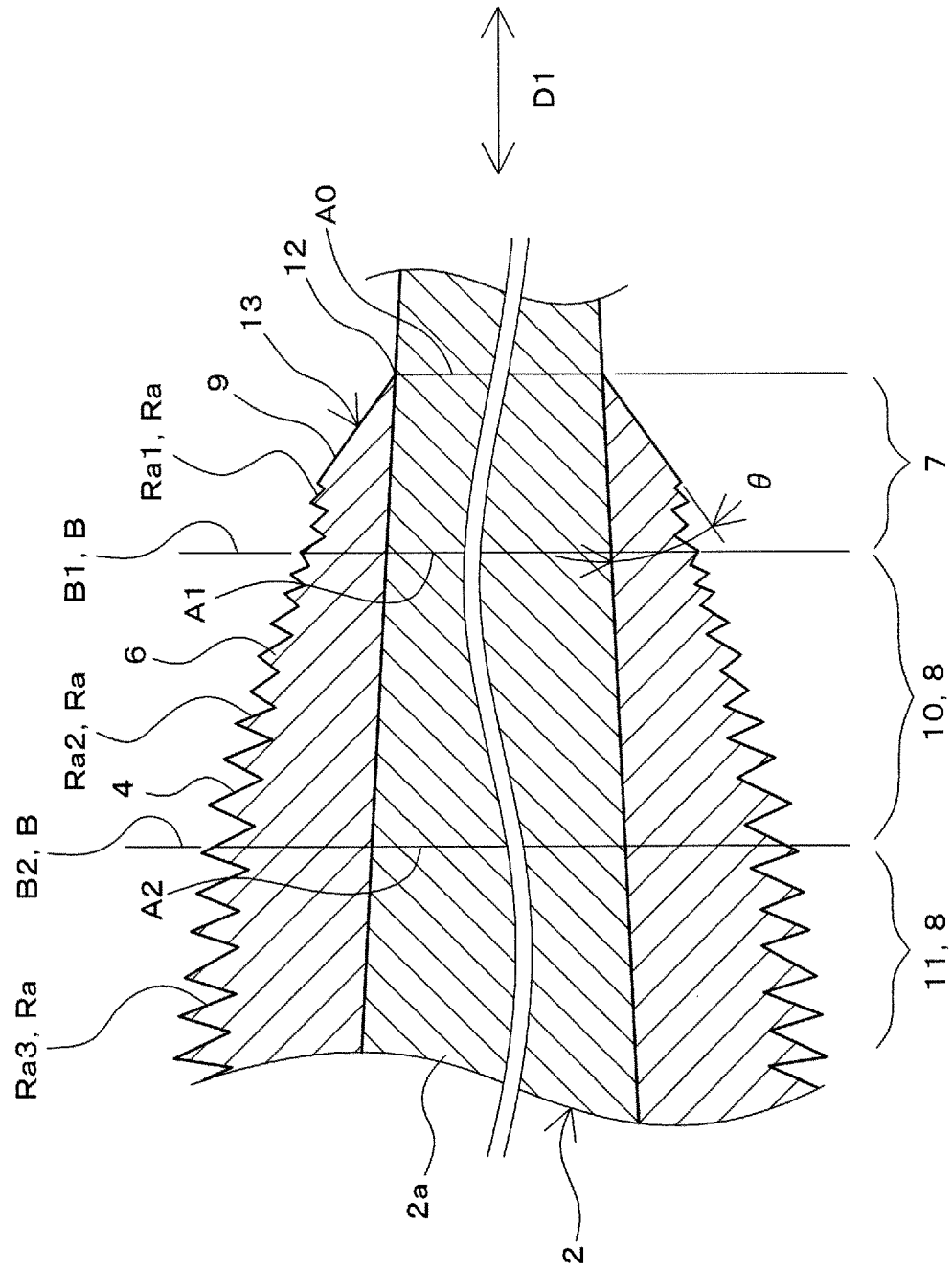
FIG. 2 is a partial view of a stem portion of the artificial joint illustrated in FIG. 1, and schematically illustrates a cross section of a roughened surface portion of the stem portion.

FIG. 2 is a partial view of the stem portion 2 of the artificial joint 1 illustrated in FIG. 1, and schematically illustrates a cross section of the roughened surface portion 4 of the stem portion 2. In FIG. 2, a cross section of a distal end-side edge portion of the roughened surface portion 4 is illustrated in an enlarged manner.

The roughened surface portion 4 is for the stem portion 2, inserted in the medullary cavity of a thigh bone, to be fixed to the bone by a frictional force. The roughened surface portion 4 is provided in the proximal end-side portion (portion closer to the proximal end opposite the distal end for insertion into the bone than to the distal end), and includes a thermally sprayed layer 6 which is formed by spraying droplets of a coating material in a molten state to the stem portion 2. The surface of the roughened surface portion 4 has fine asperities resulting from thermal spraying. The roughened surface portion 4 has a rougher surface than the distal end-side portion. Note that, in FIG. 2, the dimensions of the thermally sprayed layer 6 are illustrated in an exaggerated manner relative to those of a base member 2a covered by the thermally sprayed layer 6 of the stem portion 2, for the sake of clarity of the configuration.

In the present embodiment, as illustrated in FIG. 2, a cross section of the roughened surface portion 4, in a direction perpendicular to central axis D1 of the stem portion 2, is larger in area than a cross section of the distal end-side portion of the stem portion 2. That is, in cross sections perpendicular to the central axis D1 of the stem portion 2, the roughened surface portion 4 is larger in area than the distal end-side portion, which is not roughened, of the stem portion 2.

The thermally sprayed layer 6 at the surface of the roughened surface portion 4 is in the form of a thin layer and is disposed on the surface of the base member 2a of the stem portion 2. The thickness of the thermally sprayed layer 6, a surface roughness Ra which is the surface roughness of the thermally sprayed layer 6, and the like are adjusted by changing conditions such as the time for which the coating material in the molten state is sprayed, the temperature at which the coating material in the molten state is sprayed, and/or the pressure at which the coating material in the molten state is sprayed, when forming the thermally sprayed layer 6. Note that, in the present embodiment, the surface roughness of the thermally sprayed layer 6 is the surface roughness of the roughened surface portion 4. The surface roughness Ra, which is the surface roughness of the thermally sprayed layer 6, is, for example, calculated as arithmetic mean roughness. The thickness of the thermally sprayed layer 6, in the form of a thin layer on the surface of the base member 2a of the stem portion 2, is set to, for example, about several tens of micrometers to several hundreds of micrometers. Note that the thickness of the thermally sprayed layer 6 is configured to vary from one section to another, as illustrated in FIG. 2. For example, when a coating material in a molten state is sprayed to form a distal end-side portion of the thermally sprayed layer 6, that portion of the thermally sprayed layer 6 can be made thin by carrying out the thermal spraying only for a short time.

The thickness of a thermally sprayed layer is measured by, for example: a non-destructive measurement method such as using an optical three-dimensional shape measuring apparatus (e.g., three-dimensional shape measuring apparatus employing a light-section method) or a contact-type three-dimensional shape measuring apparatus; or a destructive measurement method involving, for example, cutting the thermally sprayed layer and the base member in a direction perpendicular to the central axis D1 of the stem portion 2 and observing the cut surface under a microscope or the like to measure the thickness. The optical three-dimensional shape measuring apparatus (e.g., three-dimensional shape measuring apparatus employing a light-section method) can be, for example, VR-3200 manufactured by keyence, and an image of an edge portion of the thermally sprayed layer can be captured in a high magnification mode (40× magnification). On the basis of the data obtained by capturing the image, the base member and the thermally sprayed layer were measured along seven lines spaced apart at 2 mm intervals, the thickness of the thermally sprayed layer and a slope angle θ (described later) were found for each of the lines, and the average was calculated. The surface roughness Ra of the thermally sprayed layer can be arithmetic mean roughness (Ra) defined in JIS B0601-2001, which can be measured by, for example, a method involving determining a cross-sectional profile using measurement data obtained by a three-dimensional shape measuring apparatus like that described above. The surface roughness Ra can alternatively be measured with use of a contact-type (contact probe) profilometer. In the present embodiment, the surface roughness Ra of the thermally sprayed layer is adjusted by adjusting conditions such as the time for which a coating material in a molten state is sprayed, the temperature at which the coating material in the molten state is sprayed, and/or the pressure at which the coating material in the molten state is sprayed. The surface roughness Ra can alternatively be adjusted by mechanical processing such as machining, grinding, sandblasting, or the like, after the thermally sprayed layer is formed. Alternatively, the surface roughness Ra can be adjusted by a chemical treatment such as etching with an acid or by a combination of such methods.

The roughened surface portion 4 includes a distal end-side edge section 7 and a proximal end-side section 8. Referring to FIG. 2, the distal end-side edge section 7 includes a distal end-side edge portion of the roughened surface portion 4. The proximal end-side section 8 is configured as a section closer to the proximal end than the distal end-side edge section 7 is to the proximal end. The stem portion 2 is inserted into the medullary cavity such that the distal end thereof enters the medullary cavity first, and then the distal end-side edge section 7 and proximal end-side section 8 enter the medullary cavity in this order. A surface roughness Ra1, which is the surface roughness of the distal end-side edge section 7 of the roughened surface portion 4 and which is calculated as arithmetic mean roughness, is set to a value less than a surface roughness (Ra2, Ra3) which is the surface roughness of the proximal end-side section 8 and which is calculated as arithmetic mean roughness. In the distal end-side edge section 7, the thermally sprayed layer 6 increases in thickness with decreasing distance to the proximal end to form a sloped surface 9.

The thermally sprayed layer 6, which is composed of a coating material and which is disposed at the surface of the roughened surface portion 4 of the stem portion 2, is a continuous layer extending over the distal end-side edge section 7 and the proximal end-side section 8. The thermally sprayed layer 6 in the distal end-side edge section 7 increases in thickness with decreasing distance to the proximal end to form the sloped surface 9.

The sloped surface 9 is present in the distal end-side edge portion of the roughened surface portion 4. The sloped surface 9 slopes downward in the direction from the proximal end toward the distal end of the roughened surface portion 4. More specifically, the sloped surface 9 forms a shape that tapers in the direction from the proximal end toward the distal end of the roughened surface portion 4. As illustrated in FIG. 2, the sloped surface 9 slopes at a slope angle θ, which is the angle between (i) the surface of the base member 2a of the stem portion 2 on which a coating material in a molten state has been sprayed and (ii) the surface of the distal end-side portion of the thermally sprayed layer 6 formed by spraying the coating material in the molten state. More specifically, the slope angle θ is an angle in a plane that includes central axis M (see FIG. 1) of the stem portion 2, and is the angle at which a thermally sprayed layer's distal portion 13 at the distal end of the thermally sprayed layer 6 slopes with respect to the surface of the base member 2a of the stem portion 2. In other words, the slope angle θ is the angle between the sloped surface 9 and the surface of the base member 2a covered by the thermally sprayed layer 6 of the stem portion 2 in a cross section perpendicular to the central axis M of the stem portion 2. Furthermore, the sloped surface 9 has a slope start point 12 at the distal end of the thermally sprayed layer's distal portion 13 at which the thermally sprayed layer 6 starts sloping upward from the surface of the base member 2a of the stem portion 2.

The proximal end-side section 8 includes a proximal end-side first section 10 and a proximal end-side second section 11. The proximal end-side first section 10 is a part of the proximal end-side section 8 which part is adjacent to the distal end-side edge section 7. The proximal end-side second section 11 is adjacent to the proximal end-side first section 10 and located on the opposite side of the proximal end-side first section 10 from the distal end-side edge section 7. The distal end-side edge section 7, the proximal end-side first section 10, and the proximal end-side second section 11 are located sequentially in the middle of the stem portion 2 in the direction from the distal end toward the proximal end. The average thickness of the thermally sprayed layer 6 in the proximal end-side first section 10 is greater than the average thickness of the thermally sprayed layer 6 in the distal end-side edge section 7, and is less than the average thickness of the thermally sprayed layer 6 in the proximal end-side second section 11.

The roughened surface portion 4 has a plurality of boundaries B in an area extending between the proximal and the distal end. A first boundary B1, which is the boundary between the distal end-side edge section 7 and the proximal end-side first section 10, is located at a position at which the total cross-sectional area of the stem portion 2 is 7% greater than the cross-sectional area of the stem portion 2 at the slope start point 12 (such a cross-sectional area, i.e., the cross-sectional area at the distal end of the thermally sprayed layer, is hereinafter referred to as "end cross-sectional area A0"). That is, the cross-sectional area A1 of the stem portion 2 at the first boundary B1 is 1.07 times the end cross-sectional area A0.

A second boundary B2, which is the boundary between the proximal end-side first section 10 and the proximal end-side second section 11, is located at a position at which the total cross-sectional area of the stem portion 2 is 25% greater than the end cross-sectional area A0. That is, the cross-sectional area A2 of the stem portion 2 at the second boundary B2 is 1.25 times the end cross-sectional area A0.

In the present embodiment, the surface roughness Ra3 of the proximal end-side second section 11 is set to a value greater than the surface roughness Ra1 of the distal end-side edge section 7. The surface roughness Ra2 of the proximal end-side first section 10 changes such that it gradually increases from a roughness of a similar level to the surface roughness Ra1 of the distal end-side edge section 7 to a roughness of a similar level to the surface roughness Ra3 of the proximal end-side second section 11 in the direction from the distal end toward the proximal end. Note that the surface roughness Ra2 of the proximal end-side first section 10 may change such that it increases stepwise from a roughness of a similar level to the surface roughness Ra1 of the distal end-side edge section 7 to a roughness of a similar level to the surface roughness Ra3 of the proximal end-side second section 11.

In the present embodiment, the slope angle θ is determined from, for example, profile data of the roughened surface portion 4 of the stem portion 2 measured by a three-dimensional shape measuring apparatus employing a light-section method. The slope angle θ is determined by: measuring the angle, at the slope start point 12, between the sloped surface 9 and the surface of the stem portion 2 in an area closer to the distal end than the thermally sprayed layer's distal portion 13 is to the distal end; and then subtracting the measured angle from 180 degrees.

Figure 3:
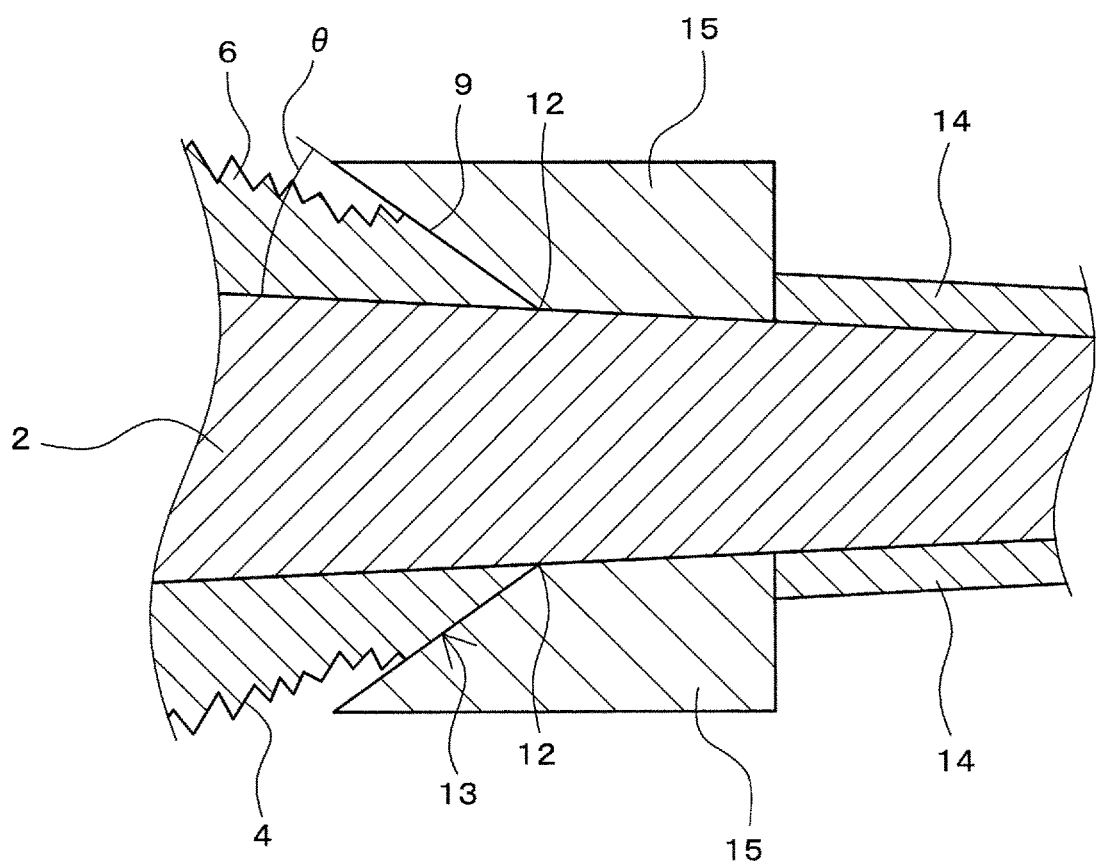
FIG. 3 is a partial view of the stem portion of the artificial joint illustrated in FIG. 1, and schematically illustrates the artificial joint in a masked state.

The thermally sprayed layer 6 is formed in the following manner: a part of the base member 2a (substrate) of the stem portion 2 is masked with a masking material (masking tape 14 and masking member 15); and a coating material in a molten state is sprayed to the surface of the base member 2a on which the masking material is disposed. FIG. 3 is a partial view of the stem portion 4 of the artificial joint 1 illustrated in FIG. 1, and schematically illustrates the artificial joint 1 in a masked state. Specifically, before the coating material in the molten state is sprayed to the stem portion 2, the masking tape 14 is wrapped around the surface of a distal end-side portion of the stem portion 2, and the masking member 15 is disposed in an area where the sloped surface 9 of the thermally sprayed layer's distal portion 13 is to be formed. The masking member 15 has a shape that fits the sloped surface 9 sloping at the slope angle θ, and (i) is shaped such that the sloped surface 9 starts sloping upward from the slope start point 12 toward the proximal end and (ii) overhangs the stem portion 2 toward the proximal end. That is, the masking material, which masks the stem portion 2, overhangs the stem portion 2 in a cross section passing through the central axis of the stem portion 2, and the sloped surface 9, sloping downward toward the distal end, is formed in the distal end-side edge portion of the roughened surface portion 4. The coating material in the molten state is sprayed to the masked stem portion 2. A thermal spraying machine for spraying the coating material in the molten state may be an arc thermal spraying machine. The thermal spraying machine may alternatively be a plasma thermal spraying machine or the like. The method of forming the sloped surface 9 is not limited to those using masking, and may be a method involving trimming the distal end-side edge of the thermally sprayed layer 6 after forming the thermally sprayed layer 6.

The production of the foregoing stem portion 2 having the roughened surface portion 4 involves a base member preparing step, a masking step, and a roughened surface portion forming step.

Specifically, the base member preparing step involves preparing the base member 2, which is to be covered by the thermally sprayed layer 6 composed of a coating material. The masking step involves partially covering the base member 2 with a masking material. The roughened surface portion forming step involves spraying the coating material in a molten state to form, in a proximal end-side portion of the stem portion, a roughened surface portion that has a rougher surface than the distal end-side portion of the stem portion 2 and that is larger in cross-sectional area than the distal end-side portion of the stem portion 2.

In particular, in the roughened surface portion forming step, the roughened surface portion is produced so that the surface roughness Ra1 of the distal end-side edge section 7 is lower than the surface roughness of the proximal end-side section 8. Specifically, the coating material in the molten state is sprayed to the distal end-side edge section 7 of the roughened surface portion 4 under the situation in which one or more of the following conditions are changed from those under which the coating material in the molten state is sprayed to the proximal end-side section 8: the time for which the coating material in the molten state is sprayed; the temperature at which the coating material in the molten state is sprayed; and the pressure at which the coating material in the molten state is sprayed.

FIG. 4 is a table showing a list of the results of a fatigue test concerning Comparative Examples and Examples of the present invention. In the present embodiment, as shown in FIG. 4, the fatigue test was carried out under the conditions shown in Comparative Examples 1 to 4 and Examples 1 to 3. In Comparative Example 1, the slope angle θ was set to 54 degrees, the surface roughness of the distal end-side edge section 7 was set to 25 μm, and the surface roughness of the proximal end-side second section 11 was set to 21 μm. In Comparative Example 2, the slope angle θ was set to 82 degrees, the surface roughness of the distal end-side edge section 7 was set to 48 μm, and the surface roughness of the proximal end-side second section 11 was set to 45 μm. In Comparative Example 3, the slope angle θ was set to 28 degrees, the surface roughness of the distal end-side edge section 7 was set to 37 μm, and the surface roughness of the proximal end-side second section 11 was set to 32 μm. In Comparative Example 4, the slope angle θ was set to 22 degrees, the surface roughness of the distal end-side edge section 7 was set to 16 μm, and the surface roughness of the proximal end-side second section 11 was set to 12 μm.

In Example 1, the slope angle θ was set to 19 degrees, the surface roughness of the distal end-side edge section 7 was set to 27 μm, and the surface roughness of the proximal end-side second section 11 was set to 53 μm. In Example 2, the slope angle θ was set to 31 degrees, the surface roughness of the distal end-side edge section 7 was set to 18 μm, and the surface roughness of the proximal end-side second section 11 was set to 47 μm. In Example 3, the slope angle θ was set to 11 degrees, the surface roughness of the distal end-side edge section 7 was set to 12 μm, and the surface roughness of the proximal end-side second section 11 was set to 51 μm.

With regard to Comparative Examples 1 and 2, the fatigue test was carried out under the conditions in which the surface roughness Ra1 of the distal end-side edge section 7 and the surface roughness Ra3 of the proximal end-side second section 11 were set to equivalent levels. The surface roughness Ra1 of the distal end-side edge section 7 and the surface roughness Ra3 of the proximal end-side second section 11 in Comparative Example 1 are set to values less than those of Comparative Example 2. With regard to Comparative Example 3, the fatigue test was carried out with under the conditions in which the slope angle θ was set to a value smaller than those of Comparative Examples 1 and 2 and in which the surface roughness Ra1 of the distal end-side edge section 7 and the surface roughness Ra3 of the proximal end-side second section 11 were set to substantially equivalent levels. With regard to Comparative Example 4, the fatigue test was carried out under the conditions in which the slope angle θ was set to a value smaller than those of Comparative Examples 1 and 2 and in which the surface roughness Ra1 of the distal end-side edge section 7 and the surface roughness Ra3 of the proximal end-side second section 11 were set to substantially equivalent levels. With regard to Examples 1 to 3, the fatigue test was carried out under the conditions in which the surface roughness Ra1 of the distal end-side edge section 7 was set to a small value, the surface roughness Ra3 of the proximal end-side second section 11 was set to a value greater than the surface roughness Ra1 of the distal end-side edge section 7, and the slope angle θ was varied.

Figure 6:
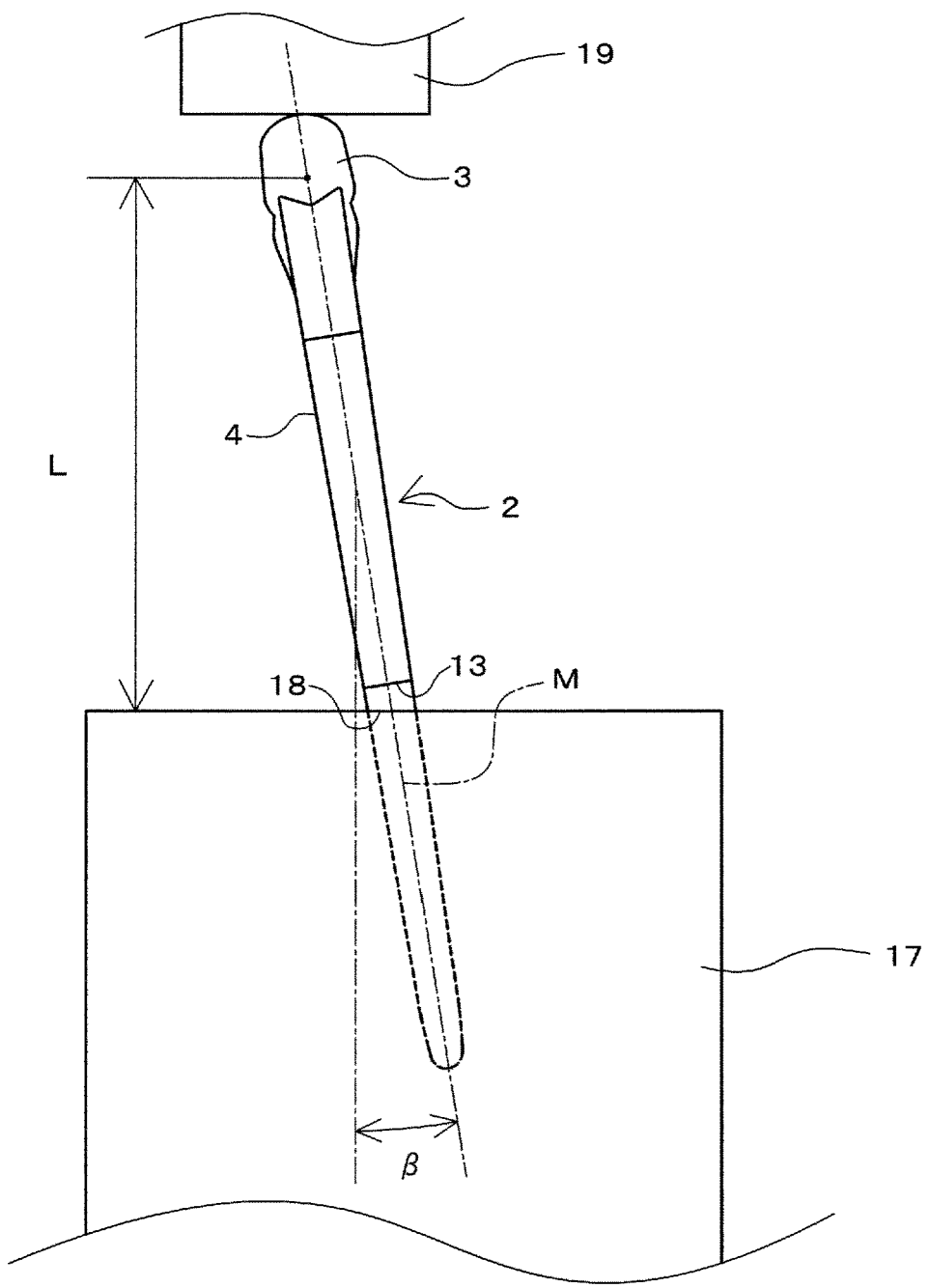
FIG. 6 illustrates the artificial joint which is set in a fatigue tester such that the artificial joint is inclined in the direction of flexion.

FIG. 5 illustrates the artificial joint 1 which is set in a fatigue tester such that the artificial joint 1 is inclined in the direction of adduction. FIG. 6 illustrates the artificial joint 1 which is set in a fatigue tester such that the artificial joint 1 is inclined in the direction of flexion. FIG. 7 is a table showing a list of the conditions in which the fatigue test was carried out. In the present embodiment, the fatigue test was carried out under the situation in which the stem portion 2 was set as illustrated in FIGS. 5 and 6, with reference to ISO7206-4:2010. Referring to FIG. 7, the fatigue test was carried out in air at room temperature. In the fatigue test, the stem portion 2 was set to a holder 17 such that the distance L from a center-of-ball 16 to a fixing end 18 (at which the stem portion 2 is fixed to the holder 17) was 90 mm. Note that the tolerance of the distance L from the center-of-ball 16 to the fixing end 18 is set to 2 mm. A fixing medium for fixing the stem portion 2 to the holder 17 used here was PMMA cement (GC ostron, Surgical Simplex). Note that the thermally sprayed layer's distal portion 13 is located higher than the fixing end 18.

In the fatigue test, the stem portion 2 is set such that the central axis thereof is inclined with respect to the holder 17. The central axis M of the stem portion 2 is set such that the central axis M is inclined, with respect to the top-to-bottom direction of the holder 17, in the direction of adduction or in the direction of flexion. More specifically, the angle at which the central axis M of the stem portion 2 is inclined with respect to the holder 17 in the direction of adduction (such an angle is hereinafter referred to as "setting angle α") is set such that the central axis M is inclined at an angle of 10 degrees to the top-to-bottom direction in the direction of adduction of a hip joint, as illustrated in FIG. 5. Furthermore, the angle at which the central axis M of the stem portion 2 is inclined with respect to the holder 17 in the direction of flexion (such an angle is hereinafter referred to as "setting angle β") is set such that the central axis M is inclined forward along the direction in which the thigh bone is bent with respect to the pelvis, i.e., inclined with respect to the to-to-bottom direction, by 9 degrees, as illustrated in FIG. 6. Note that the tolerance of the setting angle α and the tolerance of the setting angle β of the stem portion 2 are each set to 1 degree.

In the fatigue test, a sinusoidal load is applied, from above, by a pressing section 19 to the head ball portion 3 on the stem portion 2 fixed to the holder 17. The frequency of the sinusoidal load applied to the head ball portion 3 is set to 10 Hz. The sinusoidal load applied to the head ball portion 3 is set so that the load increases in stages. A certain sinusoidal load is applied a predetermined number of times in a certain stage, and then a sinusoidal load of the next magnitude is applied a predetermined number of times in the next stage. The pitch of the load applied to the head ball portion 3 is, in a case where the maximum load is less than 2.3 KN, set to 0.2 KN. In a case where the maximum load is 2.3 KN or more, the pitch of the load applied to the head ball portion 3 is set to 0.3 KN. The upper limit of the maximum load is set to 3.2 KN, and the stress ratio, which is the ratio between the maximum load and the minimum load, is set to 0.1. The repeat count, which is the number of times the load is applied to the head ball portion 3, is, in a case where the load for the test is 2.3 KN, set to five million. In a case where the load for the test is not 2.3 KN, the repeat count is set to one million.

Specifically, in the fatigue test, for example, a sinusoidal load with a maximum of 1.9 KN is first applied to the stem portion 2 one million times. Next, a sinusoidal load with a maximum of 2.1 KN is applied one million times. Next, a sinusoidal load with a maximum of 2.3 KN is applied five million times. Next, a sinusoidal load with a maximum of 2.6 KN is applied one million times. Next, a sinusoidal load with a maximum of 2.9 KN is applied one million times. Lastly, a sinusoidal load with a maximum of 3.2 KN, which is the upper limit of the maximum load, is applied one million times. Note that the lower limit of the maximum load is not limited to 1.9 KN.

In the above-stated fatigue test, the maximum load in the stage immediately preceding the stage in which the stem portion 2 was broken is referred to as "runout load". For example, in a case where the stem portion 2 was, for example, broken in the foregoing stage in which a load with a maximum of 2.6 KN was applied, the maximum load in the immediately preceding stage, 2.3 KN, is the runout load. Note that the level of the runout load, at which sufficient fatigue strength is achieved and therefore the edge portion of the roughened surface portion 4 does not need to be displaced from the area subject to stress concentration and at which there is no need to provide body weight limitation for using the artificial joint, is preferably 2.3 KN or more.

The breakage of the stem portion 2 tends to occur at or near the thermally sprayed layer's distal portion 13 of the stem portion 2 which extends from the fixing end 18 and is supported at only one end. Referring to FIG. 6, the stem portion 2 is set such that it is inclined in the direction of adduction and in the direction of flexion; therefore, in a region on the side where the angle between the central axis M of the stem portion 2 and the top surface of the holder 17 is an obtuse angle, a tensile stress results from the load applied by the pressing section 19. On the contrary, in a region on the side where the angle between the central axis M of the stem portion 2 and the top surface of the holder 17 is an acute angle, a compressive stress results from the load applied by the pressing section 19. In particular, the tensile stress and the compressive stress resulting from the applied load are concentrated in a part of the stem portion 2 which part is near the fixing end 18.

Figure 8:
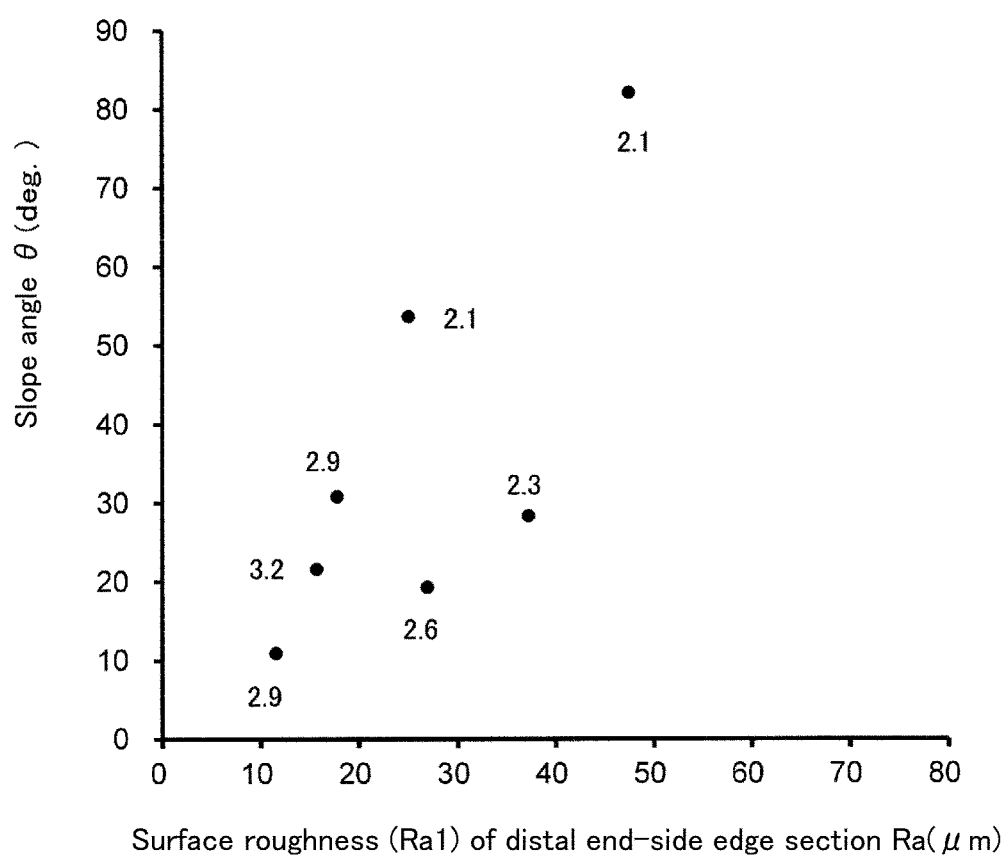
FIG. 8 is a chart showing a relationship between surface roughness and the slope angle of a thermally sprayed layer, which are the results of the fatigue test concerning Comparative Examples and Examples of the present invention.
Figure 9:
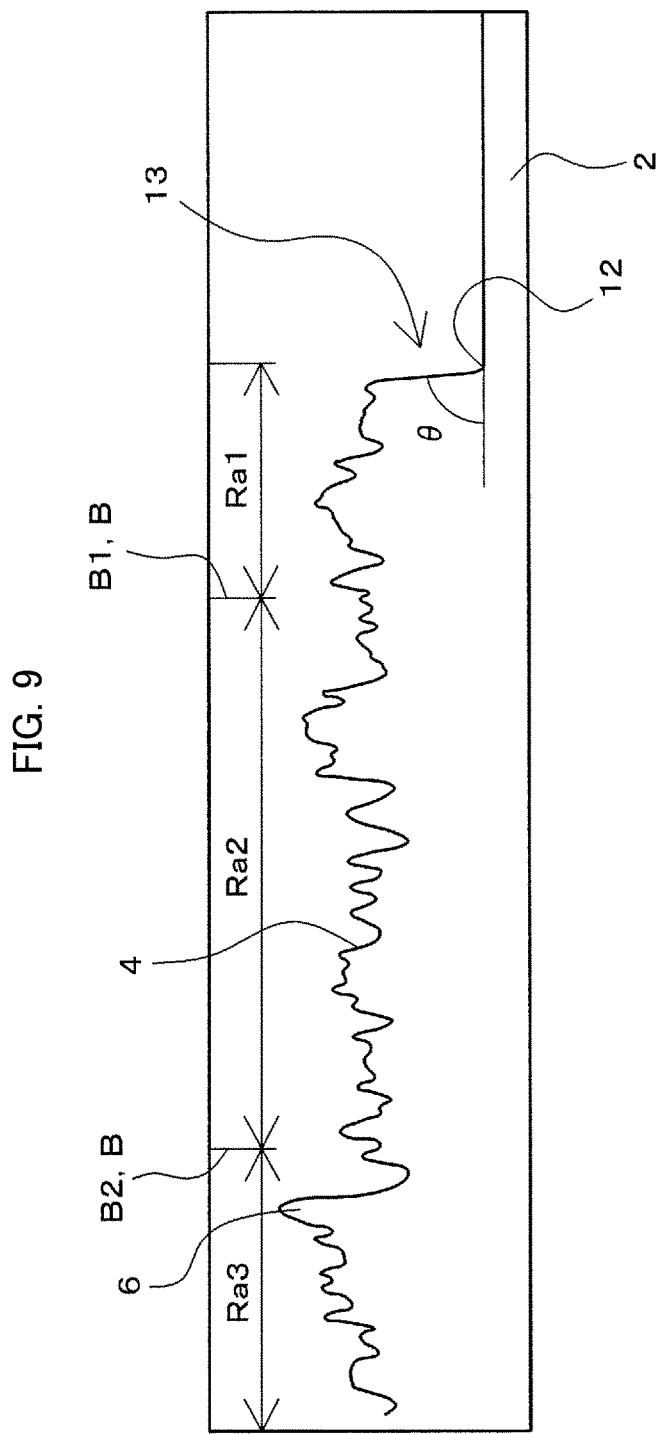
FIG. 9 is a chart showing a profile of Comparative Example 2.
Figure 10:
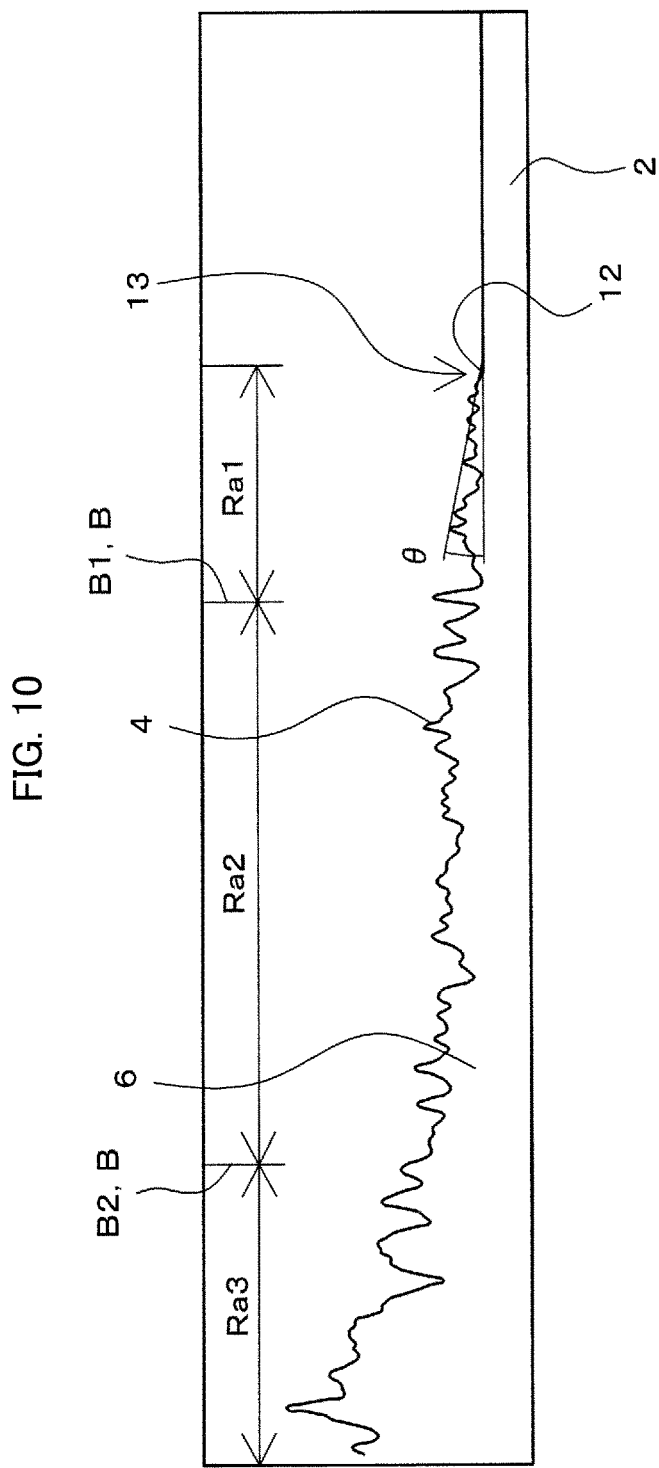
FIG. 10 is a chart showing a profile of Example 3.

FIG. 8 is a chart showing a relationship between surface roughness and the slope angle θ of the thermally sprayed layer 6, which are the results of the fatigue test concerning Comparative Examples and Examples of the present invention. The numerical values shown in the chart of FIG. 8 represent the runout loads shown in FIG. 4. FIG. 9 is a chart showing a profile of Comparative Example 2. FIG. 10 is a chart showing a profile of Example 3. Note that FIGS. 9 and 10 are examples of a cross-sectional profile based on measured data.

In Comparative Example 1, the fatigue test was carried out under the conditions in which the slope angle θ was set to 54 degrees and in which the surface roughness Ra1 of the distal end-side edge section 7 and the surface roughness Ra3 of the proximal end-side second section 11 were set to substantially equal values, i.e., 25 μm and 21 μm, respectively (see FIGS. 4 and 8). As a result, cracking started from the slope start point 12, and breakage occurred in the thermally sprayed layer's distal portion 13. The runout load was 2.1 KN.

In Comparative Example 2, the fatigue test was carried out with under the conditions in which the slope angle θ was set to 82 degrees, which was greater than that of Comparative Example 1, and in which the surface roughness Ra1 of the distal end-side edge section 7 and the surface roughness Ra3 of the proximal end-side second section 11 were set to substantially equal values, i.e., 48 μm and 45 μm, respectively (see FIGS. 4, 8, and 9). As a result, similarly to Comparative Example 1, cracking started from the slope start point 12, and breakage occurred in the thermally sprayed layer's distal portion 13. The runout load was 2.1 KN.

In Comparative Example 3, the fatigue test was carried out under the conditions in which the slope angle θ was set to 28 degrees, which was smaller than those of Comparative Examples 1 and 2, and in which the surface roughness Ra1 of the distal end-side edge section 7 and the surface roughness Ra3 of the proximal end-side second section 11 were set to substantially equal levels, i.e., 37 μm and 32 μm, respectively (see FIGS. 4 and 8). As a result, breakage occurred in the surface of the thermally sprayed layer 6 in a region where the cross-sectional area of the stem portion 2 is greater than that at the slope start point 12 of the sloped surface 9 by not more than 7%, and the runout load was 2.3 KN. In Comparative Example 3, the slope angle θ was smaller than those of Comparative Examples 1 and 2, which resulted in an improvement in runout load.

In Comparative Example 4, the fatigue test was carried out under the conditions in which the slope angle θ was set to 22 degrees and in which the surface roughness Ra1 of the distal end-side edge section 7 and the surface roughness Ra3 of the proximal end-side second section 11 were set to substantially equal levels i.e., 16 μm and 12 μm, respectively (see FIGS. 4 and 8). As a result, no breakage occurred even under a load of 3.2 KN, which is the upper limit of the maximum load. That is, the runout load was 3.2 KN, which was favorable. On the contrary, since the surface roughness Ra3 of the proximal end-side second section 11 was 12 μm, which was not set to a value greater than the surface roughness Ra1 (16 μm) of the distal end-side edge section 7, the ability to fix to a bone cannot be improved.

In Example 1, the slope angle θ was set to 19 degrees (see FIGS. 4 and 8). Then, the fatigue test was carried out under the conditions in which the surface roughness Ra1 of the distal end-side edge section 7 and the surface roughness Ra3 of the proximal end-side second section 11 were set to 27 μm and 53 μm, respectively, i.e., the surface roughness Ra3 of the proximal end-side second section 11 was greater than the surface roughness Ra1 of the distal end-side edge section 7. As a result, breakage occurred in the surface of the thermally sprayed layer 6 in a region where the cross-sectional area of the stem portion 2 is greater than that at the slope start point 12 of the sloped surface 9 by not more than 7%, and the runout load was 2.6 KN. In Example 1, the runout load was greater than 2.3 KN, and an improvement in fatigue strength was achieved. Since the surface roughness of the proximal end-side second section 11 is set to a value greater than the surface roughness of the distal end-side edge section 7 of the roughened surface portion 4, the ability to fix to a bone is also achieved.

In Example 2, the slope angle θ was set to 19 degrees (see FIGS. 4 and 8). Then, the fatigue test was carried out under the conditions in which the surface roughness Ra1 of the distal end-side edge section 7 and the surface roughness Ra3 of the proximal end-side second section 11 were set to 18 μm and 47 μm, respectively, i.e., the surface roughness Ra3 of the proximal end-side second section 11 was greater than the surface roughness Ra1 of the distal end-side edge section 7. As a result, breakage occurred in the surface of the thermally sprayed layer 6 in a region where the cross-sectional area of the stem portion 2 is greater than that at the slope start point 12 of the sloped surface 9 by not more than 7%, and the runout load was 2.9 KN. In Example 2, the runout load was greater than 2.3 KN, and the fatigue strength improved more than Example 1. Since the surface roughness of the proximal end-side second section 11 is set to a value greater than the surface roughness of the distal end-side edge section 7 of the roughened surface portion 4, the ability to fix to a bone is also achieved.

In Example 3, the slope angle θ was set to 11 degrees (see FIGS. 4, 8, and 10). Then, the fatigue test was carried out under the conditions in which the surface roughness Ra1 of the distal end-side edge section 7 and the surface roughness Ra3 of the proximal end-side second section 11 were set to 12 μm and 51 μm, respectively, i.e., the surface roughness Ra3 of the proximal end-side second section 11 was greater than the surface roughness Ra1 of the distal end-side edge section 7. As a result, breakage occurred in the surface of the thermally sprayed layer 6 in a region where the cross-sectional area of the stem portion 2 is greater than that at the slope start point 12 of the sloped surface 9 by not more than 7%, and the runout load was 2.9 KN. In Example 3, the runout load was greater than 2.3 KN, and the fatigue strength improved more than Example 1, similarly to Example 2. Since the surface roughness of the proximal end-side second section 11 is set to a value greater than the surface roughness of the distal end-side edge section 7 of the roughened surface portion 4, the ability to fix to a bone is also achieved.

It is understood from FIG. 8 that Examples 1 to 3, which are distributed in the lower left area, are greater in runout load than Comparative Example 1 to 4. That is, it is confirmed that, when the slope angle θ is small and the surface roughness Ra1 of the distal end-side edge section 7 is small, fatigue strength improves.

With regard to Comparative Example 4, although the runout load is large, the surface roughness Ra3 of the proximal end-side second section 11 is small (see FIG. 4) and the ability to fix to a bone is not achieved. The foregoing results on Examples 1 to 3 show that, as compared to Comparative Examples (which are equivalent in level to conventional products), when the slope angle θ is small and the surface roughness Ra3 of the proximal end-side second section 11 is set to a value greater than the surface roughness Ra1 of the distal end-side edge section 7, the runout load dramatically improves and the fatigue strength improves.

Furthermore, it was confirmed from the foregoing results that, in cases where the surface roughness Ra1 (arithmetic mean roughness) of the distal end-side edge section 7 is not greater than 35 μm and the surface roughness Ra3 (arithmetic mean roughness) of the proximal end-side second section 11 is not less than 40 μm, the occurrence of cracking and breakage and the like can be further avoided and a greater ability of the stem portion to fix to a bone is achieved. Furthermore, it is apparent from these results that, in cases where the surface roughness Ra1 (arithmetic mean roughness) of the distal end-side edge section 7 is not greater than 35 μm and the surface roughness (arithmetic mean roughness) of the proximal end-side section 8 is not less than 40 μm, the occurrence of cracking and breakage and the like can be further avoided and a greater ability of the stem portion to fix to a bone is achieved.

Thus, an artificial joint that can improve fatigue strength while achieving the ability to fix to a bone was obtained.

Action and Effect of the Present Embodiment

The stem portion 2 of the artificial joint 1 in accordance with the present embodiment includes the roughened surface portion 4, which has a rough surface. When the stem portion 2 of the artificial joint 1 is inserted into a bone, the stem portion 2 is fixed by a frictional force. Furthermore, the roughened surface portion 4 is configured such that the distal end-side edge section 7 has a lower surface roughness than that of the proximal end-side section 8. With this, the artificial joint 1 in accordance with the present embodiment makes it possible, as compared to a conventional artificial joint 1 which is not configured such that the surface roughness is low in the distal end-side edge portion, to avoid the occurrence of cracking and breakage and the like in the distal end-side edge portion of the roughened surface portion 4. This makes it possible to improve fatigue strength. Furthermore, the edge portion of the roughened surface portion 4 does not need to be displaced, and there is no need to provide body weight limitation for using the artificial joint. Since the artificial joint 1 configured as described above is configured such that the roughness of the proximal end-side section 8 is greater than that of the distal end-side edge section 7, a sufficient ability to fix to a bone can also be achieved.

Thus, it is possible to provide a stem portion 2 of an artificial joint 1 that can improve fatigue strength while achieving the ability to fix to a bone.

Furthermore, with regard to the stem portion 2 of the artificial joint 1, the sloped surface 9 is provided in the distal end-side edge portion of the roughened surface portion 4 such that the sloped surface 9 slopes downward toward the distal end. With this, the distal end of the roughened surface portion 4 does not have a stepped shape, and it is possible to further alleviate the concentration of stress in the edge portion of the roughened surface portion 4. As a result, the occurrence of cracking and breakage and the like in the roughened surface portion 4 of the artificial joint 1 are further avoided.

Furthermore, with regard to the stem portion 2 of the artificial joint 1, the proximal end-side section 8 includes the proximal end-side first section 10 and the proximal end-side second section 11, the proximal end-side first section 10 is adjacent to the distal end-side edge section 7, and the proximal end-side second section 11 is adjacent to the proximal end-side first section 10 and is located on the opposite side of the proximal end-side first section 10 from the distal end-side edge section 7. Furthermore, the surface roughness of the proximal end-side first section 10 changes such that it gradually increases from a roughness of a similar level to the surface roughness of the distal end-side edge section 7 to a roughness of a similar level to the surface roughness of the proximal end-side second section 11. Thus, the surface roughness of the roughened surface portion 4, in the direction from the distal end toward the proximal end, is gradually changed instead of being abruptly changed, which makes it possible to avoid stress concentration. This makes it possible to improve fatigue strength while achieving the ability to fix to a bone.

Furthermore, with regard to the stem portion 2 of the artificial joint 1, the roughened surface portion 4 includes the thermally sprayed layer 6 composed of a coating material. That is, the thermally sprayed layer 6 is formed by spraying the coating material in a molten state. Furthermore, in the distal end-side edge section 7 of the roughened surface portion 4, the thermally sprayed layer 6 increases in thickness with decreasing distance to the proximal end to form the sloped surface 9. By changing conditions in which the coating material in a molten state is sprayed, it is possible to form the thermally sprayed layer 6 which has an adjusted thickness. Therefore, it is possible to easily form, in the roughened surface portion 4, the sloped surface 9 sloping at an angle suitable for need, by adjusting thickness.

Furthermore, with regard to the stem portion 2 of the artificial joint 1, the slope angle θ, which is the angle between the surface of the base member 2a of the stem portion 2 covered by the thermally sprayed layer 6 and the surface of the distal end-side portion of the thermally sprayed layer 6, is not more than 45 degrees. This makes it possible to further alleviate the concentration of stress in the edge portion of the roughened surface portion 4 that would otherwise result from a large slope angle θ. As a result, the occurrence of cracking and breakage and the like in the roughened surface portion 4 of the artificial joint 1 are further avoided.

Furthermore, with regard to the stem portion 2 of the artificial joint 1, the surface roughness Ra1, calculated as arithmetic mean roughness, of the distal end-side edge section 7 is not more than 35 μm. This makes it possible to further avoid the occurrence of cracking and breakage and the like in the distal end-side edge portion of the roughened surface portion 4. Furthermore, the surface roughness, calculated as arithmetic mean roughness, of the proximal end-side section 8 is not less than 40 μm, that is, the surface roughness of the proximal end-side section 8 is set to a value greater than the surface roughness of the distal end-side edge section 7. This makes it possible to achieve a greater ability of the stem portion 2 to fix to a bone.

Furthermore, with regard to the stem portion 2 of the artificial joint 1, the stem portion 2 contains a titanium alloy and/or pure titanium. Therefore, because of the high strength and biocompatibility of a titanium alloy or pure titanium, a more suitable artificial joint 1 can be obtained.

The artificial joint 1 in accordance with the present invention is, for example, an implant of an artificial hip joint for a thigh bone. An implant for an artificial hip joint in accordance with the present invention is an artificial joint 1 which, after implanted in the human body, receives a large load repeatedly during, for example, ambulation activity. In this regard, the following advantage, which is a characteristic of the present invention, can be further utilized: fatigue strength can be improved while achieving the ability to fix to a bone.

A method of producing an artificial joint in accordance with the present embodiment includes: a base member preparing step including preparing a base member 2a of a stem portion 2; a masking step including placing a masking material on a part of the base member 2; and a roughened surface portion forming step in which a coating material in a molten state is sprayed to a proximal end-side portion of the stem portion 2 to form a roughened surface portion 4 which has a rougher surface than a distal end-side portion. That is, the stem portion 2 of the artificial joint 1 includes the roughened surface portion 4 which has a rough surface. The roughened surface portion 4 can be produced such that the surface roughness Ra1 of the distal end-side edge section 7 is lower than that of the proximal end-side section 8. This makes it possible to appropriately produce an artificial joint 1 that has improved fatigue strength and achieves the ability to fix to a bone.

In the method of producing an artificial joint, in the masking step, the masking material masks the stem portion 2 so as to overhang the stem portion 2, and the sloped surface 9 sloping downward toward the distal end is formed in the distal end-side edge portion of the roughened surface portion 4. That is, it is possible to provide, in the distal end-side edge portion of the roughened surface portion 4, a sloped surface 9 sloping downward toward the distal end. This makes it possible to provide an artificial joint 1 in which the occurrence of cracking, breakage, and the like in the roughened surface portion 4 are further avoided.

[Variations]

An embodiment of the present invention has been discussed so far. Note, however, that the present invention is not limited to the foregoing embodiment, and may be modified in various ways within the scope of the claims. For example, the present invention can be modified as described below.

(1) Although an example case in which the surface of the artificial joint 1 according to an artificial hip joint is roughened was discussed in the foregoing embodiment, this does not imply any limitation. For example, a configuration in which the surface of an artificial joint according to a shoulder joint is roughened may be employed.

(2) Although a case in which the surface of the stem portion 2 of the artificial joint 1 is roughened by thermal spraying was discussed in the foregoing embodiment, this does not imply any limitation. For example, the following configuration may be employed: the surface of the roughened surface portion 4 of the stem portion 2 of the artificial joint 1 is one that has been mechanically roughened by cutting, grinding, shot blasting, or the like; or a roughened surface portion is formed by so-called additive manufacturing such as additive fabrication.

(3) Although the artificial joint 1 whose stem portion 2 and head ball portion 3 are integral with each other was discussed in the foregoing embodiment, this does not imply any limitation. For example, the following configuration may be employed: a stem portion (part) 2 of the artificial joint 1 has a neck portion; and a head ball portion (part) 3, which is a separate part, is fitted in the neck portion.

INDUSTRIAL APPLICABILITY

The present invention can be widely applied as an artificial joint 1 to be placed in the medullary cavity of a bone and a method of producing the artificial joint.

REFERENCE SIGNS LIST 1 artificial joint
2 stem portion
4 roughened surface portion
6 thermally sprayed layer
7 distal end-side edge section
8 proximal end-side section
9 sloped surface
10 proximal end-side first section
11 proximal end-side second section

The invention claimed is:

1. An artificial joint comprising including a stem portion, the stem portion having a distal end for insertion into a bone, and a proximal end opposite the distal end, the stem portion comprising:
   a roughened surface portion which is closer to the proximal end than the distal end,
   wherein the roughened surface portion has a distal end-side edge section and a proximal end-side section, and has a cross-sectional area at the proximal end-side section that is larger than a cross-sectional area at the distal end-side edge section,
   wherein a surface roughness of the distal end-side edge section is smaller than a surface roughness of the proximal end-side section, wherein the distal end-side edge section of the roughened surface portion has a sloped surface sloping downward toward the distal end, wherein:

the roughened surface portion includes, at a surface thereof, a thermally sprayed layer composed of a coating material; and in the distal end-side edge section, the thermally sprayed layer increases in thickness with decreasing distance to the proximal end to form the sloped surface.

2. The artificial joint as set forth in claim 1, wherein:

the proximal end-side section includes a proximal end-side first section that is adjacent to the distal end-side edge section, and a proximal end-side second section that is adjacent to the proximal end-side first section and is located on an opposite side of the proximal end-side first section from the distal end-side edge section; and a surface roughness of the proximal end-side first section gradually increases, in a direction from the distal end toward the proximal end, from a roughness of a similar level to the surface roughness of the distal end-side edge section, to a roughness of a similar level to a surface roughness of the proximal end-side second section.

3. The artificial joint as set forth in claim 1, wherein a slope angle between a surface of a base member being covered by the thermally sprayed layer, and a surface of the distal end-side edge section of the thermally sprayed layer is not more than 45 degrees.

4. The artificial joint as set forth in claim 1, wherein:

an arithmetic mean of the surface roughness of the distal end-side edge section is not greater than 35 μm; and an arithmetic mean of the surface roughness of the proximal end-side section is not less than 40 μm.

5. The artificial joint as set forth in claim 1, wherein the stem portion contains a titanium alloy and/or pure titanium.

6. The artificial joint as set forth in claim 1, wherein the artificial joint is an implant of an artificial hip joint for a thigh bone.

* * * * *